(12) United States Patent
Belov

(10) Patent No.: US 9,391,002 B2
(45) Date of Patent: Jul. 12, 2016

(54) SEMICONDUCTOR SENSOR CHIPS

(71) Applicant: Amphenol Thermometrics, Inc., Saint Marys, PA (US)

(72) Inventor: Nickolai S. Belov, Schenectady, NY (US)

(73) Assignee: Amphenol Thermometrics, Inc., Saint Marys, PA (US)

(*) Notice: Subject to any disclaimer, the term of this patent is extended or adjusted under 35 U.S.C. 154(b) by 0 days.

(21) Appl. No.: 14/086,259

(22) Filed: Nov. 21, 2013

(65) Prior Publication Data

US 2015/0137274 A1    May 21, 2015

(51) Int. Cl.
| | |
|---|---|
| H01L 23/48 | (2006.01) |
| H01L 23/00 | (2006.01) |
| G01L 9/00 | (2006.01) |
| G01L 19/00 | (2006.01) |

(52) U.S. Cl.
CPC ............ *H01L 23/481* (2013.01); *G01L 9/0054* (2013.01); *G01L 19/0076* (2013.01); *G01L 19/0092* (2013.01); *H01L 24/09* (2013.01); *H01L 24/49* (2013.01); *H01L 24/45* (2013.01); *H01L 2224/45015* (2013.01); *H01L 2224/45147* (2013.01); *H01L 2224/49* (2013.01); *H01L 2924/00014* (2013.01); *H01L 2924/0105* (2013.01); *H01L 2924/01013* (2013.01); *H01L 2924/01032* (2013.01); *H01L 2924/01049* (2013.01); *H01L 2924/01079* (2013.01); *H01L 2924/01322* (2013.01); *H01L 2924/12042* (2013.01)

(58) Field of Classification Search
CPC ....... H01L 23/481; H01L 24/09; H01L 24/49; G01L 9/0054; G01L 19/0076; G01L 19/0092
See application file for complete search history.

(56) References Cited

U.S. PATENT DOCUMENTS

| | | | |
|---|---|---|---|
| 6,125,291 | A | 9/2000 | Miesel et al. |
| 6,393,907 | B1 | 5/2002 | Yamakawa et al. |
| 6,603,183 | B1 | 8/2003 | Hoffman |

(Continued)

OTHER PUBLICATIONS

Belov, N., et al., "Thin-Layer Au—Sn Solder Bonding Process for Wafter-Level Packaging, Electrical Interconnections and MEMS Applications," Interconnect Technology Conference (2009), IITC 2009. IEEE International, pp. 128-130.

(Continued)

*Primary Examiner* — Long Pham
(74) *Attorney, Agent, or Firm* — Blank Rome LLP

(57) ABSTRACT

Semiconductor sensor chips are provided. In some embodiments, a semiconductor sensor chip can include at least one wire bond pad on one side thereof, at least one bond pad on another, opposite side thereof, and at least one through-silicon via (TSV) extending therebetween and electrically connected to the bond pads on opposite sides of the chip. Each of the bond pads can have a wire attached thereto. In some embodiments, a semiconductor sensor chip can include a pressure sensor, a substrate, and a resistor in a well that provides p-n junction isolation from a body of the substrate. In some embodiments, a semiconductor sensor chip can include a plurality of wire bonds pads with a wire soldered to each of the bond pads. Each of the wires can be soldered with a longitudinal length thereof soldered to its associated bond pad.

16 Claims, 4 Drawing Sheets

(56) References Cited

U.S. PATENT DOCUMENTS

| | | |
|---|---|---|
| 2002/0003274 A1 | 1/2002 | Bryzek et al. |
| 2002/0156417 A1 | 10/2002 | Rich et al. |
| 2004/0040382 A1 | 3/2004 | Peterson et al. |
| 2005/0187487 A1 | 8/2005 | Azizkhan et al. |
| 2007/0052077 A1 | 3/2007 | Wathanawasam et al. |
| 2008/0027332 A1* | 1/2008 | Bradley ............... A61B 5/0215 600/485 |
| 2008/0255647 A1 | 10/2008 | Jensen et al. |
| 2009/0039527 A1* | 2/2009 | Chan ................. H01L 27/14618 257/777 |
| 2012/0313207 A1 | 12/2012 | Oganesian |
| 2013/0237864 A1* | 9/2013 | Mazar .................. A61B 5/0215 600/488 |

OTHER PUBLICATIONS

International Search Report issued in PCT/US2014/066604 on Feb. 12, 2015.

* cited by examiner

SEMICONDUCTOR SENSOR CHIPS

FIELD

The subject matter disclosed herein relates to semiconductor sensor chips, such as semiconductor sensor chips for catheters.

BACKGROUND

Pressure sensor chips can be used in a variety of applications to sense and measure pressure. In some applications, a pressure sensor chip must be relatively small in order to fit within a space in which pressure needs to be measured. For example, pressure sensor chips used in catheters can measure pressure of a fluid surrounding a catheter. The catheters can be used for pressure measurements in medical applications. For example, blood pressure inside a heart can be monitored using a catheter, such as during complex surgeries or heart tests. The catheters can be used in industrial applications to measure fluid pressure, e.g., gas pressure or liquid pressure. Pressure sensor dies for catheter applications, also referred to herein as a "catheter pressure sensor die" and a "catheter die," must have a size smaller than an inner diameter of the catheter in order to be able to fit within the catheter's passageway. Long wires are located inside the catheter for signal transfer from the pressure sensor die to an external device.

One problem with traditional pressure sensor chips is that the smaller a pressure sensor chip, the more difficult it is for the pressure sensor chip to accurately sense pressure since the chip has a smaller pressure sensing element (e.g., diaphragm) and, therefore, has lower sensitivity to applied pressure. By having a smaller size, the pressure sensor chip has less room for wire connectivity thereto, which can mean fewer wires (e.g., three or less) connected thereto, a lower sensitivity to applied pressure, a higher signal to noise ratio, and/or yield loss at assembly due to difficulties with wire connection. The chip can therefore provide less accurate pressure measurements and can have a higher cost.

Another problem with traditional pressure sensor chips is that in applications using long wires, such as in catheter applications, the wires have to be connected securely to the chip such that the wires do not become loose and/or detached during assembly and/or during use. In order to simplify manufacturing and to provide enough wire connection strength, some traditional pressure sensor chips are placed on a substrate/die holder. A chip and substrate/die holder is also referred to herein as a "sub-assembly." Short wires can be connected to the pressure sensor chip and the substrate/die holder to help ensure that the wires do not become loose or detached from the pressure sensor chip. Long wires attached to the substrate/die holder can connect the sub-assembly to an external device.

FIG. 1 shows one example of a traditional pressure sensor chip 176 on a substrate/die holder 178 with wires 180, 182 connected thereto via wire bonds. Ends of the wires 180, 182 are wire bonded to the chip 176, and portions of the wires 180, 182 near the ends are wire bonded to the substrate/die holder 178. The connection to the substrate/die holder 178 helps absorb any force applied to the wires 180, 182 so that the wire ends attached to the chip 176 can remain securely attached to the chip 176. However, including the substrate/die holder 176 increases an overall size of the sub-assembly, which can make it more difficult to use the sub-assembly in applications where small size is important. For example, including a substrate/die holder in catheter applications means that the catheter must have a diameter large enough to accommodate the catheter die and the substrate/die holder. FIG. 2 demonstrates this adverse affect by showing the chip 176 and the substrate/die holder 178 within a passageway 184 of a catheter 186.

Another problem with traditional pressure sensor chips is that wires connected to the chip via wire bonding each require the use of a bond pad having at least a minimum size and a minimum spacing between the bond pads. The minimum size is related to a diameter of the wire used for wire bonding, and the minimum spacing between bond pads is related to the size of tooling used at wire bonding. The bond pads can therefore require that the pressure sensor chip have a certain minimum size, namely a certain minimum width, which may still be too large for certain applications. If bond pads are made too small, the reliability of the wire bonds decreases. Wire bonding also causes a loop of wire to extend above the bond pads on the pressure sensor chip's surface, which can require additional space inside the catheter passageway and, therefore, increase a minimum inner diameter of the catheter and, hence, an overall size of the system. For example, FIGS. 1 and 2 show loops caused by the wires 180, 182 that are wire bonded to the chip 176. FIG. 2 also demonstrates how the catheter 186 must be sized to accommodate the loops.

Additionally, if a pressure sensor chip includes components for sensing other parameters such as temperature and pH, bond pads and wires for these other components can occupy valuable chip real estate. Real estate limitations on the chip make it difficult to accommodate a required number of bond pads on the chip.

Accordingly, there remains a need for improved semiconductor sensor chips.

BRIEF DESCRIPTION

Semiconductor sensor chips are generally disclosed herein. In one embodiment, a sensing device is provided that includes a catheter die. The catheter die can include a top side and a bottom side defining a thickness of the catheter die, and a first side and a second side defining a width of the catheter die. Each of the first and second sides can extend between the top and bottom sides. The catheter die can also include a first end and a second end defining a length of the catheter die, a sensor component located on the top side, a first bond pad on the top side, a second bond pad on the bottom side, and a through-silicon via extending between the bottom and top sides and electrically connected to the first and second pads. The first pad can be electrically connected to the sensor component and have a first wire attached thereto, and the second pad can be electrically connected to the sensor component and have a second wire attached thereto. The first and second wires can be configured to facilitate sensing functionality of the sensor component.

In another embodiment, a sensing system includes a catheter die and a catheter tube. The catheter die can have a first bond pad on a first exterior side thereof, a first wire attached to the first pad, a second bond pad on a second exterior side thereof that is opposite to the first exterior side, a second wire attached to the second bond pad, at least one sensor component, and a through-silicon via extending between the first and second exterior sides electrically connected to the first and second bond pads. The first and second wires can facilitate a pressure sensing capability of the catheter die. The catheter tube can have a lumen extending longitudinally therethrough. The catheter die can be disposed entirely within the lumen. The first and second wires can extend off the catheter die and can extend longitudinally through the lumen.

In another aspect, a semiconductor system is provided. In one embodiment a semiconductor system includes a conductive substrate having a first type of conductivity and being configured to contact an external media, a sensor resistor having the first type of conductivity, and an isolation area between the sensor resistor and the conductive substrate. The isolation area can have a second type of conductivity. The system can also include a first p-n junction formed between the isolation area and the conductive substrate, and a second p-n junction formed between the sensor resistor and the isolation area. A combination of the first p-n junction and the second p-n junction can be configured to provide electrical isolation of the sensor resistor from an electrical potential of the external media. When an electrical potential is applied to the isolation area during sensor operation, the electrical potential can keep the second p-n junction closed and the first p-n junction can provide electrical isolation of the sensor resistor from the electrical potential of the external media.

In another embodiment, a semiconductor system includes a semiconductor die that includes a diaphragm, a top side, a bottom side, and side walls extending between the top and bottom sides. The top side, the bottom side, and the side walls can be configured to be in contact with an external media. The system can also include at least one P-type piezoresistor disposed on the diaphragm, an N-well surrounding the p-type piezoresistor, a P-type substrate surrounding the N-well, a first p-n junction formed between the N-well and the P-type substrate, and a second p-n junction formed between the P-type piezoresistor and the N-well. The N-well can have no exposure to the side walls. The side walls can not be protected with a dielectric layer, the external media can have an electrical potential, and a combination of the first p-n junction and the second p-n junction can be configured to provide electrical isolation of the at least one P-type piezoresistor from an electrical potential of the external media.

In yet another embodiment, a semiconductor system includes a sensor die. The sensor die can include a device layer having side walls configured to contact an external media, a handle layer, a dielectric layer that electrically isolates the device layer from the handle layer without protecting the side walls of the device layer, and a sensor resistor having a first type of conductivity and formed in the device layer. The sensor die can also include an isolation area having the first type of conductivity and formed in the device layer along the side walls, a first p-n junction formed between the isolation area and a body of the device layer, and a second p-n junction formed between the sensor resistor and the body of the device layer. The body of the device layer can have a second type of conductivity. The body of the device layer can be a remainder portion of the device layer that does not include the isolation area and does not include the sensor resistor. A combination of the first p-n junction, the second p-n junction, and the dielectric layer can be configured to provide electrical isolation of the sensor resistor from an electrical potential of the external media that is in contact with the side walls.

BRIEF DESCRIPTION OF THE DRAWING

These and other features will be more readily understood from the following detailed description taken in conjunction with the accompanying drawings, in which.

Figure 1:
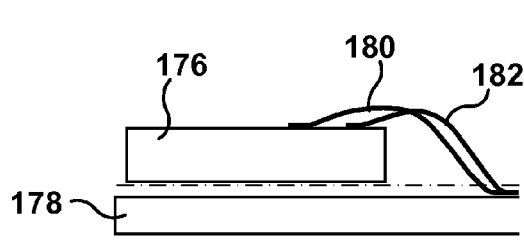
FIG. 1 (Prior Art) is a side view of an assembly including a catheter die, a substrate/die holder, and wires attached to the catheter die and the substrate/die holder.
Figure 2:
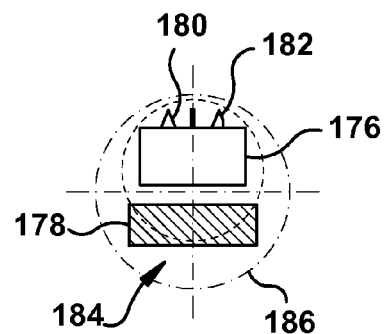
FIG. 2 (Prior Art) is an end view of the assembly of FIG. 1 disposed in a passageway of a catheter.

It is noted that the drawings are not necessarily to scale. The drawings are intended to depict only typical aspects of the subject matter disclosed herein, and therefore should not be considered as limiting the scope of the disclosure. In the drawings, like numbering represents like elements between the drawings.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary semiconductor sensor chips are provided. In general, the semiconductor sensor chips can be configured to sense a parameter, such as pressure of an external element, e.g., a fluid.

The devices, systems, and methods disclosed herein produce a number of advantages and/or technical effects.

In some embodiments, a semiconductor sensor chip can include at least one bond pad for wire connection on one side thereof, at least one bond pad for wire connection on another, opposite side thereof, and at least one through-silicon via (TSV) electrically connecting the bond pads on opposite sides of the chip. Each of the bond pads can have a wire attached thereto. The wires can facilitate sensing functionality, e.g., pressure sensor functionality, of the chip. Having bond pads on opposite sides of the chip can allow the chip to have a relatively small size, which can conserve valuable real estate for other elements in sensing applications and/or can allow the chip to be used in very tight spaces. Using a TSV can allow a plurality of wires to be attached on one or on both sides of the chip, which can provide improved sensor sensitivity. In some embodiments, the chip can have four wires attached thereto so as to provide a full Wheatstone bridge formed by four sensing components, for example, four resistors. A full Wheatstone bridge provides higher sensitivity to the measured parameter, e.g., pressure, as compared to sensitivity provided by less than four sensing components, e.g., than a similar sensor die having two resistors and three wires. Traditional semiconductor sensor chips, particularly those of small size such as pressure sensor chips used in catheter applications, often include only two piezoresistors kept on the die with the other two resistors being connected externally to form the Wheatstone bridge circuit. Including only two resistors can help reduce a size of the die, but it limits the self-contained capability of the die.

In some embodiments, a semiconductor sensor chip can include a mechanical structure for pressure sensing (e.g., a diaphragm), a substrate having the mechanical structure formed thereon, and at least one sensing component, e.g., one or more piezoresistors. The piezoresistor(s) can be located fully or partially on the mechanical structure for pressure sensing. Pressure applied to the mechanical structure can result in mechanical stress and change of the resistance of the piezoresistor(s). This change can be detected by a sensor circuit, such as a Wheatstone bridge circuit. The piezoresistor(s) can be located inside a volume of semiconductor material having a different type of conductivity than the piezoresistor. For example, the piezoresistor can have p-type conductivity and the volume can have n-type conductivity. The volume surrounding the piezoresistor is also referred to herein as a "well." The well can provide isolation of the piezoresistor(s) from a body of the substrate, which can have the same type of conductivity as the piezoresistor(s), with two p-n junctions. One p-n junction can be formed between the sensor resistor and the well, and the other p-n junction can be formed between the well and the body of the substrate. When the semiconductor sensor chip is used in an application that allows for direct contact of the sensor chip with an external media, such a configuration can minimize direct current from the chip into the external media when voltage is supplied to the chip and the external media also has some electrical potential, in other words when the chip is "on." The sensor chip can therefore have good stability, as the pressure sensitive electrical component(s), e.g., the piezoresistor(s), can be electrically isolated from an external media. The external media can thus be protected from damage that could be caused by the voltage supplied to the chip. For example, when the external media is internal body fluid and/or internal body tissue of a patient, such as when the chip is implanted or temporarily placed within a patient, preventing current flow from the chip to the patient can help prevent patient injury and/or patient discomfort.

A person skilled in the art will appreciate that the same type of electrical isolation of a sensor chip from external media with two p-n junctions can be used for sensors of other than pressure parameters and for sensors utilizing pressure sensing components other than resistor sensitive components.

In some embodiments, a semiconductor sensor chip can include a plurality of wire bond pads with a wire soldered to each of the bond pads. Each of the wires can be soldered with a longitudinal length thereof soldered to its associated bond pad. Soldering wires to bond pads allows more area of wire-to-pad connection than traditional wire-pad attachment techniques such as wire bonding and thermocompression. Having a larger connection area can help provide reliability of the wire-to-pad connection, e.g., 3×-5× time stronger than traditional wire bonding and thermocompression, especially in case of small diameter wires. Soldering wires to bond pads can be secure enough that the wires need not be also attached to a substrate, e.g., the chip need not include a substrate. Instead, long wires can be directly attached to the sensor die. Soldering wires to bond pads can facilitate longitudinal extension of the wires from the chip. The wires can be soldered to the bond pads with their trailing ends extending longitudinally off the chip, which can help the wires extend substantially parallel to one another off the chip. Such extension can help, for example, to minimize an inner diameter of a catheter tube in which the sensor die is located since wires do not have a loop extending upward from the bond pads as in case of wire bonding. Soldering wires to bond pads, and having bond pads on opposite sides of the chip connected together with a TSV, can help allow the chip to have a plurality of wires, e.g., four or more, attached thereto while also allowing the chip to have a relatively small size.

The sensor chips disclosed herein can be used in a variety of applications, such as medical applications (e.g., procedures, treatment, etc. in areas such as cardiology, gastroenterology, etc.), and industrial manufacturing applications. For example, medical applications can include applications in which one or more parameters such as pressure, pH, etc. associated with a patient are measured, and industrial manufacturing applications can include applications in which one or more parameters such as temperature, pressure, etc. is sensed. In an exemplary embodiment, a semiconductor sensor chip can be a catheter die configured to be disposed within a catheter tube in a lumen extending longitudinally through the catheter tube. The pressure sensor chip can be configured to sense a pressure of a fluid surrounding the catheter tube. Because the semiconductor sensor chip can be very small, the semiconductor sensor chip can be configured to be disposed within many different sizes of catheter tubes, including catheter tubes having very small diameters. Such very small diameter catheter tubes can be particularly useful in cardiac applications in which catheter tubes are often relatively small and are trending within the cardiac treatment community to be smaller and smaller.

The semiconductor sensor chips disclosed herein can include one or more other types of sensing functionality. For example, a semiconductor sensor chip can include any one or more of a pressure sensor, a temperature sensor, a pH sensor, a magnetic sensor, a radiation sensor, a photosensor, and a chemical sensor. The semiconductor sensor chip can thus be more versatile when in use by being configured to provide data regarding a plurality of different parameters and/or can allow one sensing device to be used instead of multiple sensing devices, which can help reduce monetary cost and/or can help conserve real estate that can be left open or used for other devices. Additionally, in some embodiments, the sensor chips disclosed herein need not include pressure sensing functionality, e.g., lack a pressure sensor, but can include one or more other types of sensing functionality, e.g., can include one or more of a temperature sensor, a pH sensor, a magnetic sensor, a radiation sensor, a chemical sensor, etc.

Figure 3:
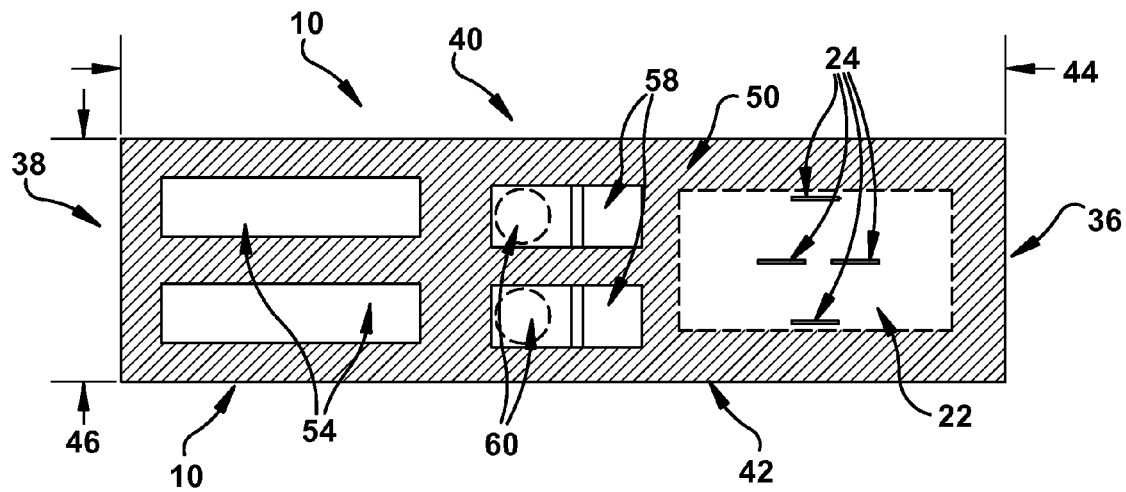
FIG. 3 is a top view of one embodiment of a pressure sensor chip.
Figure 4:
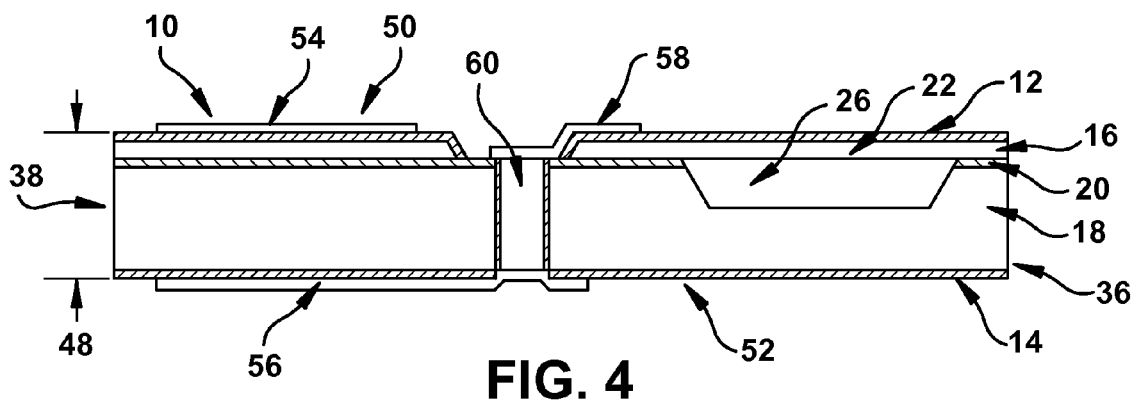
FIG. 4 is a side cross-sectional view of the pressure sensor chip of FIG. 3.

FIGS. 3 and 4 illustrate an embodiment of a semiconductor sensor chip in the form of a sensor chip 10. The chip 10 can be configured to be disposed within a lumen of a catheter tube (not shown) and to be used as a catheter die. However, the chip 10 can be used in other applications.

The chip 10 can have a rectangular box shape, as shown in the illustrated embodiment. The chip 10 can have first and second short sides 36, 38 and first and second long sides 40, 42. A length 44 of the chip 10 can be defined by a distance between the first and second short sides 36, 38. A width 46 of the chip 10 can be defined by a distance between the first and second long sides 40, 42. A thickness 48 of the chip 10 can be defined by a distance between a top or proximal side 50 of the chip 10 and a bottom or distal side 52 of the chip 10.

The chip 10 can include a top or proximal dielectric layer 12, that defines the top or proximal side 50 of the chip 10, and an opposite bottom or distal dielectric layer 14, that defines the bottom or distal side 52 of the chip 10. The proximal and distal dielectric layers 12, 14 are shown as single layers in FIG. 4, but as will be appreciated by a person skilled in the art, one or both of the proximal and distal dielectric layers 12, 14 can include multiple layers, and one or both of the proximal and distal dielectric layers 12, 14 can have a pattern that does not cover whole surfaces of the sides 50, 52 of the chip 10. The chip 10 can also include a device layer 16 just distal to the proximal dielectric layer 12 and a handle layer 18 just proximal to the distal dielectric layer 14. A buried oxide (BOX) layer 20 can be disposed between the device layer 16 and the handle layer 18. A thin diaphragm 22 can be formed within the device layer 16 over a cavity 26. A side of the diaphragm 22 facing the cavity 26 can be either covered by a dielectric film, for example the BOX layer 20, as in the illustrated embodiment, or the side of the diaphragm 22 facing the cavity 26 can be free of dielectric film.

One or more sensing components 24, e.g., piezoresistors, can be formed at the diaphragm 22. The chip 10 in the illustrated embodiment includes four pressure sensitive components 24, but a pressure sensor chip can include any number of pressure sensitive components. The sensing components 24 can include any one or more of piezoresistors, bipolar transistors, metal oxide semiconductor (MOS) transistors, complementary metal oxide semiconductor (CMOS) transistor pairs, unipolar transistors, diodes, and other electrical components, as will be appreciated by a person skilled in the art. Pressure sensitive components can be connected to a pressure sensitive circuit.

The cavity 26 can be formed within the chip 10, e.g., formed in the handle layer 18 or formed in both in the handle layer 18 and the device layer 16. The device layer 16 can seal the cavity 26, thus forming the thin diaphragm 22 over the cavity 26. The cavity 26 can be kept under vacuum or filled with a gas having a reference pressure at a reference temperature. In some embodiments, a majority portion of the cavity 26 can be formed in the handle layer 18. In some embodiments, the diaphragm 22 can have a profile that improves linearity of the output signal and sensitivity of the pressure sensor. For example, the diaphragm 22 can have one rigid island (not shown) in a center thereof or two rigid islands (not shown) parallel to each other.

The diaphragm 22 can be a flexible member configured to bend in response to an external stimulus, e.g., in response to pressure exerted thereon. The diaphragm 22 can thus bend so as to move in and out of the cavity 26.

The chip 10 can include one or more bond pads. The bond pad(s) can be located on the proximal side 50 of the chip 10, on the distal side 52 of the chip 10, or on both the proximal and distal sides 50, 52. In an exemplary embodiment, the chip 10 can have at least one bond pad 54 on the proximal side 50 and at least one bond pad 56 on the distal side 52. In an exemplary embodiment, at least one of the proximal and distal sides 50, 52 has a plurality of bond pads thereon. By having one or more bond pads 54, 56 on each of the proximal and distal sides 50, 52, the chip 10 can have more bond pads than if bond pads are only on one side of the chip 10 since surface area on two sides of the chip 10 can be used for bond pads instead of surface area on just one side of the chip 10. Consequently, the chip 10 can have more sensing components 24 sensitive to pressure and/or other parameters if bond pads are on both the proximal and distal sides 50, 52 than if bond pads are only on one of the sides 50, 52. The more pressure sensing components 24 a chip 10 has, the more sensitive, and hence the more accurate and reliable, its pressure measurements.

The chip 10 can include heavily doped P+ areas, N+ areas, or poly-Si areas (not shown) connecting the sensing component(s) 24 to the bond pads 54, 56.

Each of the bond pads 54, 56 can be configured to have a wire (not shown) attached thereto. In an exemplary embodiment, each of the wires is identical to one another. The wires can each be made from a variety of materials. In an exemplary embodiment, each the wires can be copper (Cu) wires coated by gold (Au) or coated by Au/Sn (gold/tin alloy). The wires can also have a variety of sizes, e.g., a diameter in a range of about 25 to 75 μm. By having bond pads 54, 56 having wires attached thereto on both the proximal and distal sides 50, 52 of the chip 10, an overall size of the chip 10 can be smaller than if a same number of wires were attached to a chip having bond pads on only one side thereof, e.g., only on a proximal side thereof. As will be appreciated by a person skilled in the art, one wire can be used as a power supply for the sensing component(s) 24, one wire can be used as a ground wire, and a remaining number of wires can be used as signal wires, e.g., for communicating sensed data.

The wires can be attached to the bond pads 54, 56 in a variety of ways. For example, the wires can be wire bonded, welded, attached using thermocompression, glued with an electrically conductive adhesive, or soldered to the bond pads 54, 56. For soldering, the wires can be soldered to their respective bond pads 54, 56, such as by using AuIn solder, AuSn solder, and other low-temperature solders. For example, Au—In form eutectic below 160° C. and Au—Sn form eutectic at 280° C. The solder can be deposited on the bond pads 54, 56 electrochemically, e.g., in a wafer-level process, or the solder can be deposited locally on the wires. The wires can be soldered simultaneously to their respective bond pads 54, 56. Alternatively, wires can be soldered first to bond pads located on one side of the chip 10, e.g., the proximal side 50, and then wires can be soldered to bond pads located on the other side, e.g., the distal side 52. The wires can be soldered to their respective bond pads 54, 56 by having a longitudinal length thereof soldered to their respective bond pads 54, 56. Further description of using AuSn for making mechanical connection is described in more detail in Belov et al., "Thin-Layer Au—Sn Solder Bonding Process for Wafer-Level Packaging, Electrical Interconnections and MEMS Applications," IEEE International Interconnect Technology Conference 2009, pages 128-130, which is hereby incorporated by reference in its entirety. In an exemplary embodiment, all of the wires attached to the chip 10 can be attached to their respective bond pads 54, 56 using the same technique, e.g., all soldered. A total number of the bond pads 54, 56 can equal a total number of the wires, when only one wire is attached to each one of the bond pads 54, 56.

In some embodiments, solder can be deposited on the proximal bond pads 54, and no solder can be deposited on the distal bond pads 56. Correspondingly, different methods of wire attachment can be used for the proximal and distal bond pads 54, 56. For example, wires can be soldered to the proximal bond pads 54 and can be glued to the distal bond pads 56.

The chip 10 can include one or more additional pads 58, such as wafer probing pads (probe pads). The additional pad(s) 58 can all be on a same side of the chip 10, e.g., the proximal side 50. Each of the additional pad(s) 58 can be electrically connected both to at least one of the sensing components 24 and to at least one through-silicon via (TSV) 60. Each of the TSVs 60 can extend through at least a partial depth of the chip's thickness 48. The TSVs 60 can each be formed in the handle layer 18 and can extend along a full depth thereof, as shown in FIG. 4. Alternatively, a TSV can be formed in the device layer 16 only and connected to the body of the handle layer 18 through an opening in the BOX layer 20.

The additional pads 58 as probe pads can allow for electrical access during probing to the components connected to the pads located on the distal side 52 of the chip 10. The chip 10 in the illustrated embodiment includes two additional pads 58 and two TSVs 60, but a chip can include another number of probe pads and TSVs. The TSV(s) 60 can be configured to electrically connect the proximal bond pads 54 and the distal bond pads 56, which can facilitate pressure sensing capability of the sensing component(s) 24 by facilitating cooperation of all the wires in providing pressure data to an external device (not shown). In other words, each TSV 60 can be configured to connect one node of the pressure sensitive circuit formed in the device layer 16, e.g., the proximal bond pads 54, to the distal bond pads 56. For example, there are four nodes in a closed Wheatstone bridge circuit. These nodes can correspond to four bond pads. At least one of the four bond pads can be located on the proximal side 50 of the chip 10 and a remainder of the bond pads can be located on the distal side 52 of the chip 10.

As shown in FIGS. 3 and 4, the diaphragm 22, the cavity 26, and the sensing component(s) 24 can be located nearer the first short side 36 of the chip 10 than to the second short side 38 of the chip 10. The bond pads 54, 56, the wires, and the additional pad(s) 58 can be located nearer the second short side 38 of the chip 10 than to the first short side 36 of the chip 10. The diaphragm 22, the cavity 26, and the sensing component(s) 24 can all be located nearer the first short side 36 of the chip 10 than all of the bond pads 54, 56, the wires, the additional pad(s) 58, and the TSV(s) 60. Such positioning of the bond pads 54, 56, the wires, the additional pad(s) 58, and the TSV(s) 60 can help ease assembly of the chip 10 and facilitate use of the chip 10. The positioning of the bond pads 54, 56 can help prevent the wires from interfering with the sensing of a parameter of interest, e.g., pressure, by the sensing component(s) 24, since trailing ends of the wires attached to the bond pads 54, 56 can extend from the second short side 38 of the chip 10 and extend away from the first short side 36 of the chip 10.

The pads 54, 56 and any wires attached thereto can be coated by a protective coating, for example, by epoxy or by gel. The protective coating can protect the pads 54, 56 and the wires from media so as to avoid parasitic electrical connections and/or chemical/electrochemical corrosion. In an exemplary embodiment, no portion of the diaphragm 22 is coated with a protective coating because such a coating would adversely affect both sensitivity of the sensor to pressure and stability of the sensor.

As shown in FIG. 3, the chip 10 in this illustrated embodiment allows separating the areas on the proximal side 50 occupied by sensing elements (e.g., the diaphragm 22 and the sensing components 24) and the areas on the proximal side 50 occupied by interconnecting elements (e.g., the proximal bond pads 54, the probe pads 58, the TSVs 60, and the wires (not shown)).

Figure 5:
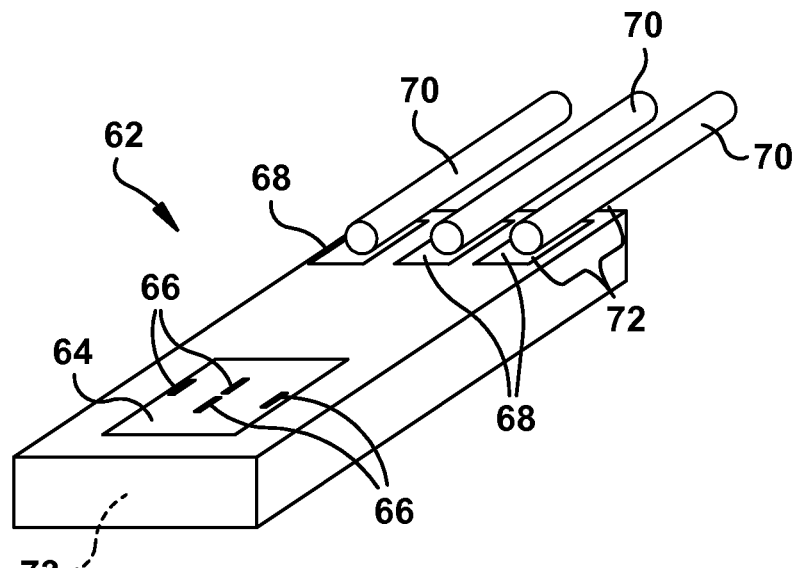
FIG. 5 is a perspective view of another embodiment of a pressure sensor chip, the chip having three wires attached thereto.

FIG. 5 shows another embodiment of a semiconductor sensor chip 62. The chip 62 can include a thin diaphragm 64, one or more pressure sensing components 66, one or more bond pads 68, and a wire 70 attached to each of the bond pad(s) 68. In an exemplary embodiment, the chip 62 can include at least two pressure sensing components 66. In this illustrated embodiment, the chip 62 includes four pressure sensing components 66, three wires 70, and three bond pads 68. The chip 62 need not include any TSVs because the chip 62 only has bond pads 68 and wires 70 on one side thereof.

The pressure sensing components 66 are piezoresistors in the illustrated embodiment, but as mentioned above, any stress-sensitive component other than piezoresistors can be used. Stress affects mobility of the carriers in semiconductor materials. Therefore, parameters of both bipolar and MOS transistors can be affected by stress. As transistors are three-pole components (in contrast with piezoresistors, which are two-pole components), complex stress-sensitive circuits can be built using a combination of transistors and resistors as the pressure sensing components 66 placed in the diaphragm area 64 and other areas of the chip 10. Transistors and other electronic components (e.g., resistors, diodes, capacitors, and inductors) can be used to pre-process signals generated by the pressure sensing components 66. In particular, a signal generated in response to pressure by a Wheatstone bridge can be amplified, and the differential output of the resistive bridge can be converted to a signal proportional to pressure that can be transferred using just one signal wire. For example, potential of the signal wire with respect to the ground can be proportional to the measured pressure. As a result, the chip 62 can have only three wires as shown in the embodiment of FIG. 5.

Each of the wires 70 is soldered to their respective bond pads 68 in this illustrated embodiment. A longitudinal length 72 of each of the wires 70 (only labeled for one of the wires 70 in FIG. 5, for clarity of illustration) can be soldered to their respective bond pads 68. In an exemplary embodiment, the longitudinal length of the wire 70 soldered can include a longitudinal length of the wire 70 at one of the wire's free ends. In this way, a first longitudinal length of the wire 70 can be soldered to the chip 62, e.g., to one of the bond pads 68, and a remaining longitudinal length trailing from the first longitudinal length can trail off the chip 62. The remaining longitudinal length of the wire 70 can trail away from the portion of the chip 62 that includes the diaphragm 64 and the pressure sensing component(s) 66, as shown in FIG. 5, which as mentioned above can help prevent the wires 70 from interfering with the chip's pressure sensing capabilities. The first longitudinal lengths of the wires 70 attached to their respective bond pads 68 can extend substantially parallel to a longitudinal axis 73 of the chip 62. In other words, the first longitudinal lengths of the wires 70 can extend substantially parallel to long sides of a rectangular-shaped chip, as is the chip 62 of FIG. 5.

The chip 62 can be configured to be disposed within a lumen of a catheter tube (not shown) and to be used as a catheter die. The trailing ends of the wires 70 can extend longitudinally through the lumen. The first longitudinal lengths of each of the wires 70 soldered to the bond pads 68 can help guide the trailing ends to extend longitudinally through the lumen.

The wires 70 can be individual wires or can be combined in a micro-cable with multiple ones of the wires 70 in the micro-cable. A number of wires in the micro-cable can correspond to a number of the bond pads 68 or can be different. For example, the micro-cable can have the wires 70 therein and can have additional wires therein that can be attached to a different sensor chip disposed in the same catheter as the chip 62.

Although not shown in FIG. 5, the chip 62 can include one or more bond pads on an opposite side thereof than the top or proximal side that includes the bond pads 68 and the wires 70. For example, in addition to the three wires 70 attached to chip 62 as shown, the chip 62 could include three bond pads on the bottom or distal side thereof, with each of the three bond pads having a wire attached thereto, e.g., by soldering. The chip 62 could thus have a total of six wires.

Figure 6:
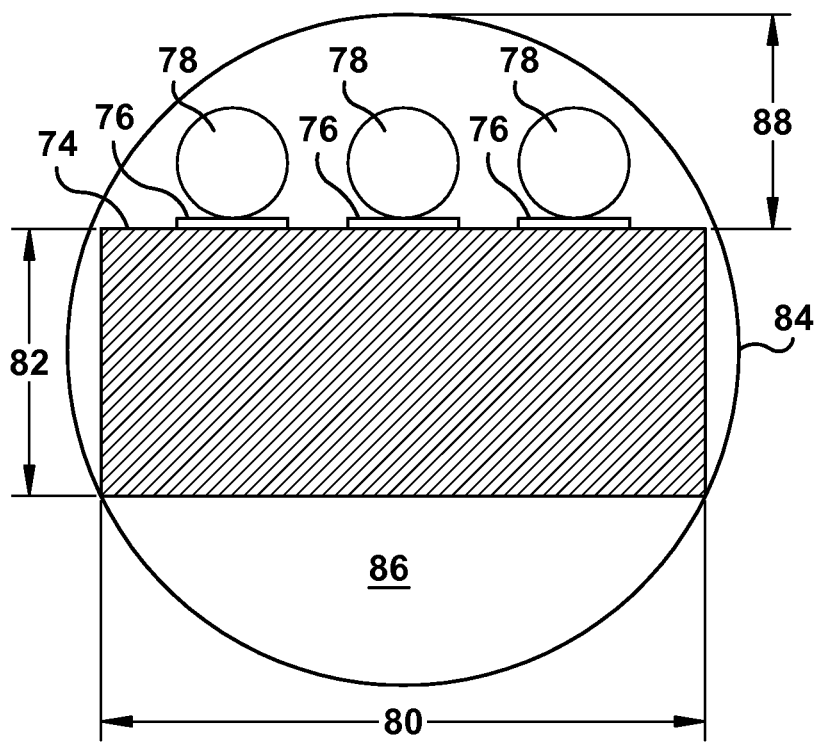
FIG. 6 is a side cross-sectional view of one embodiment of a sensor chip disposed within an inner lumen of one embodiment of a catheter tube, the chip having three wires attached thereto that extend longitudinally through the catheter tube.

FIG. 6 shows another embodiment of a semiconductor sensor chip 74. The chip 74 can include one or more bond pads 76 and a wire 78 attached to each of the bond pad(s) 76. In this illustrated embodiment, the chip 74 includes three wires 78 and three bond pads 76 that, similar to the chip 62 of FIG. 5, are arranged on a top or proximal side of the chip 62.

In one embodiment, the chip 74 can be configured to be disposed within a lumen 86 of a catheter tube 84. The chip 74 can thus be used as a catheter die.

The chip 74 in this illustrated embodiment has a width 80 of about 270 μm and a thickness 82 of about 120 μm. A person skilled in the art will appreciate that measurements of a chip may not be precisely at a certain value, e.g., be exactly 270 μm, but can be considered to be about that certain value because of, for example, tolerances allowed in manufacturing. A diameter of the lumen 86 in this illustrated embodiment is about 300 μm. Thus, a maximum height 88 within the lumen 86 available for the wires 78 attached to the chip 74 is about 96 μm. Additional data for the chip 74 and the catheter tube 84 is shown in the Table below.

| | Inner diameter of catheter, μm | | |
|---|---|---|---|
| Parameter | 400 | 300 | 250 |
| Die size, μm | 330 × 180 | 270 × 120 | 235 × 70 |
| Spacing for wires on top of the die, μm | <132 | <96 | <97 |
| Thickness of wire + layer connecting it to pad, μm | 100 max | 60 max | 60 max |
| Possible pad size, μm | 70 | 50 | 70 |
| Possible spacing between pads, μm | 30 | 30 | 35 |

Figure 7:
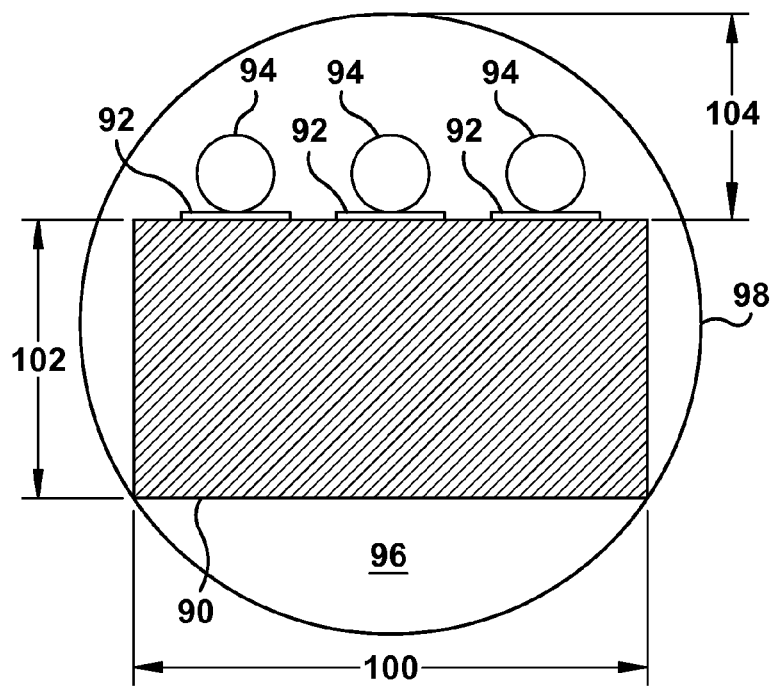
FIG. 7 is a side cross-sectional view of another embodiment of a sensor chip disposed within an inner lumen of another embodiment of a catheter tube, the chip having three wires attached thereto that extend longitudinally through the catheter tube.

FIG. 7 shows another embodiment of a semiconductor sensor chip 90. The chip 90 can include one or more bond pads 92 and a wire 94 attached to each of the bond pad(s) 92. In this embodiment, the chip 90 includes three wires 94 and three bond pads 92 that, similar to the chip 62 of FIG. 5 and the chip 74 of FIG. 6, are arranged on a top or proximal side of the chip 90.

In one embodiment, the chip 90 can be configured to be disposed within a lumen 96 of a catheter tube 98. The chip 90 can thus be used as a catheter die.

The chip 90 in this illustrated embodiment has a width 100 of about 330 μm and a thickness 102 of about 180 μm. A diameter of the lumen 96 in this illustrated embodiment is about 400 μm. Thus, a maximum height 104 within the lumen 96 available for the wires 94 attached to the chip 90 is about 96 μm. Additional data for the chip 90 and the catheter tube 98 is shown in the Table above.

Figure 8:
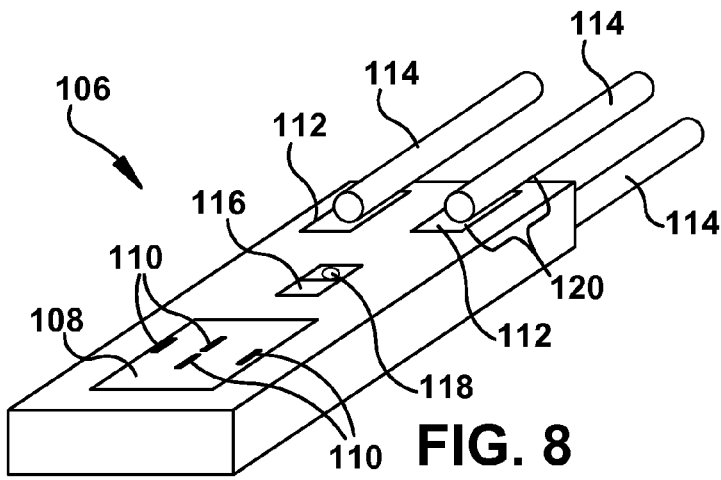
FIG. 8 is a perspective view of another embodiment of a pressure sensor chip, the chip having three wires attached thereto.

FIG. 8 shows another embodiment of a semiconductor sensor chip 106. The chip 106 can include a thin diaphragm 108, one or more pressure sensing components 110, one or more bond pads 112, a wire 114 attached to each of the bond pad(s) 112, one or more probe pads 116, and one or more TSVs 118. In this illustrated embodiment, the chip 106 includes four pressure sensing components 110, three wires 114, and three bond pads 112. One of the bond pads 112 (the one on a bottom or distal side of the chip 106) is obscured in FIG. 8.

Each of the wires 114 is soldered to their respective bond pads 112 in this illustrated embodiment. A longitudinal length 120 of each of the wires 114 (only labeled for one of the wires 114 in FIG. 8, for clarity of illustration) can be soldered to their respective bond pads 112, similar to that discussed above regarding the wires 78 of FIG. 6.

The dimensions (e.g., length, thickness, width) of the chip 106 can be the same as the dimensions of the chip 62 of FIG. 5. The wires 114 attached to the chip 106 of FIG. 8 can be larger, e.g., have a larger diameter, than the wires 70 attached to the chip 62 of FIG. 5 while still providing the chip 106 with three wires 114 because instead of having three wires on the top or proximal side of the chip 106, only two of the wires 114 are on the top or proximal side of the chip 106. The width of the chip 106 of FIG. 8 can be less than the width of the chip 62 of FIG. 5 while using the same size wires 114 as the wires 70.

The chip 106 can be configured to be disposed within a lumen of a catheter tube (not shown) and to be used as a catheter die. The trailing ends of the wires 114 can extend longitudinally through the lumen. The longitudinal lengths of each of the wires 114 soldered to the bond pads 112 can help guide the trailing ends to extend longitudinally through the lumen.

Figure 9:
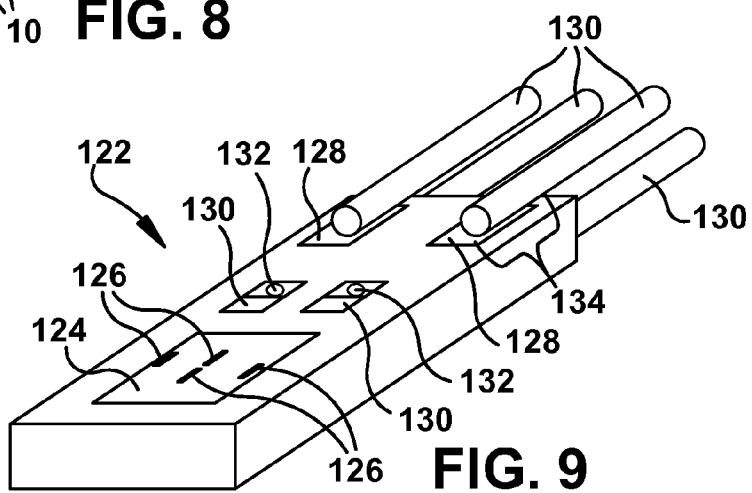
FIG. 9 is a perspective view of another embodiment of a pressure sensor chip, the chip having four wires attached thereto.

FIG. 9 shows another embodiment of a semiconductor sensor chip 122. The chip 122 can include a thin diaphragm 124, one or more pressure sensing components 126, one or more bond pads 128, a wire 130 attached to each of the bond pad(s) 128, one or more probe pads 130, and one or more TSVs 132. In this illustrated embodiment, the chip 122 includes four pressure sensing components 126, four wires 130, and four bond pads 128. Two of the bond pads 128, the two on a bottom or distal side of the chip 122, are obscured in FIG. 9.

Each of the wires 130 is soldered to their respective bond pads 128 in this illustrated embodiment. A longitudinal length 134 of each of the wires 130 (only labeled for one of the wires 130 in FIG. 9, for clarity of illustration) can be soldered to their respective bond pads 128, similar to that discussed above regarding the wires 78 of FIG. 6.

The dimensions (e.g., length, thickness, width) of the chip 122 can be the same as the dimensions of the chip 62 of FIG. 5. Thus, the wires 130 attached to the chip 122 of FIG. 9 can be larger, e.g., have a larger diameter, than the wires 70 attached to the chip 62 of FIG. 5 while providing the chip 122 with a greater number of wires because instead of having three wires on the top or proximal side of the chip 106, two of the wires 114 are on the top or proximal side of the chip 122 while two are on the bottom or distal side of the chip 122. The dimensions of the chip 122 can, however, differ from the dimensions of the chip 62 of FIG. 5. For example, the width of the chip 122 of FIG. 9 can be less than the width of the chip 62 of FIG. 5 while using the same size wires 130 as the wires 70. Similarly, the width of the chip 122 of FIG. 9 can be the same as the width of the chip 106 of FIG. 8 while using the same size wires 130 as the wires 114, yet providing more wires 130 than in the embodiment of FIG. 8.

The chip 122 can be configured to be disposed within a lumen of a catheter tube (not shown) and to be used as a catheter die. The trailing ends of the wires 130 can extend longitudinally through the lumen. The longitudinal lengths of each of the wires 130 soldered to the bond pads 128 can help guide the trailing ends to extend longitudinally through the lumen.

Figure 10:
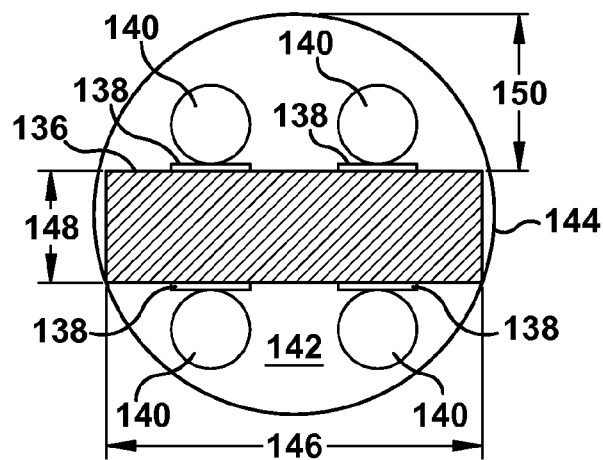
FIG. 10 is a side cross-sectional view of another embodiment of a sensor chip disposed within an inner lumen of another embodiment of a catheter tube, the chip having four wires attached thereto that extend longitudinally through the catheter tube.

FIG. 10 shows another embodiment of a semiconductor sensor chip 136. The chip 136 can include one or more bond pads 138 and a wire 140 attached to each of the bond pad(s) 138. In this embodiment, the chip 136 includes four wires 140 and four bond pads 138 that, similar to the chip 122 of FIG. 9, are arranged with two on a top or proximal side of the chip 136 and two on a bottom or distal side of the chip 136.

In one embodiment, the chip 136 can be configured to be disposed within a lumen 142 of a catheter tube 144. The chip 136 can thus be used as a catheter die.

The chip 136 in this embodiment has a width 146 of about 235 μm and a depth 148 of about 70 μm. A diameter of the lumen 142 in this embodiment is about 250 μm. Thus, a maximum height 150 within the lumen 142 available for the wires 140 attached to the proximal side of the chip 136 is about 97 μm. Similarly, a maximum height (not labeled in FIG. 10) within the lumen 142 available for the wires 140 attached to the distal side of the chip 136 is about 97 μm. Additional data for the chip 136 and the catheter tube 144 is shown in the Table above. Although the catheter tube 144 of FIG. 10 is smaller than the catheter tubes 84, 98 of FIGS. 6 and 7, a greater number of wires are disposed therein and extend longitudinally therethrough since wires are attached to both top and bottom sides of the chip 136.

Additional sensor functionality can be added to an existing semiconductor sensor chip by adding one or more sensing components and one or more wire connections to an opposite side of the chip that already has pressure sensing wires attached thereto. In other words, traditional pressure sensor chips that may have bond pads on one side thereof can have one or more bond pads retrofitted on an opposite side of the chip from the side that has the existing wires. One or more TSVs can be added. The added sensing component(s) can use the same ground wire as the pressure sensor, can use the same power supply wire as the pressure sensor, and can use one or more added signal wires. By way of example, a temperature sensor can be added as a diode or a thermistor, e.g., thin film or solid state resistor, connected in series with the existing pressure sensing circuit.

Figure 11:
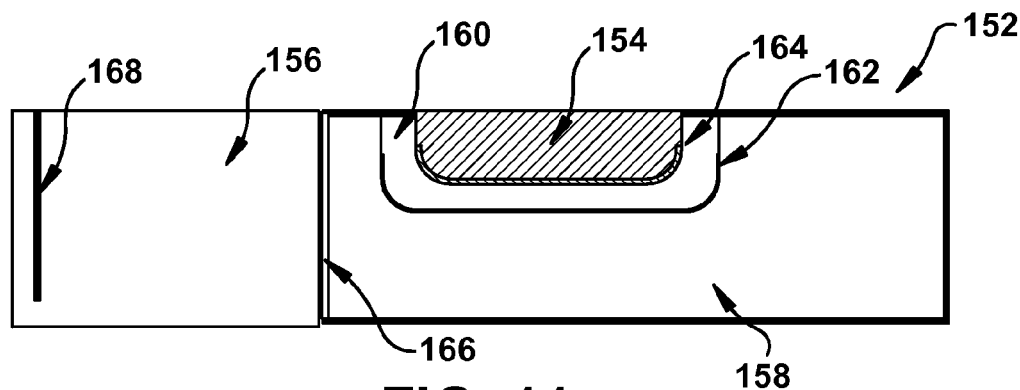
FIG. 11 is a side cross-sectional view of a system including a partial portion of one embodiment of a pressure sensing chip that is in direct contact with a conductive media.
Figure 12:
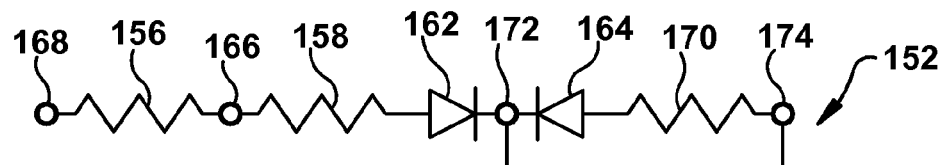
FIG. 12 is a schematic representation of the system of FIG. 11.

A semiconductor sensor chip can be configured to isolate one or more sensing components thereof, e.g., pressure sensitive components, from an external media that can have an electrical potential affecting stability of the sensor signal. FIGS. 11 and 12 illustrate an embodiment of a portion of a semiconductor sensor chip 152 configured to isolate one or more sensitive components 154 thereof from an external media 156. Some features of the chip 152 are not shown for clarity of illustration, e.g., bond pads, TSVs, etc.

The chip 152 can include the pressure sensing components 154, a substrate 158, and an isolation area 160 such as an N-well. The substrate 158 and the pressure sensing components 154 can have a first type of conductivity (n-type or p-type), and the isolation area 160 can have a second type of conductivity (the other of n-type or p-type). As a result, a first p-n junction 162 can be formed between the substrate 158 and the isolation area 160, and a second p-n junction 164 can be formed between the isolation area 160 and the pressure sensing components 154. The media 156 can be conductive and can be in contact with a remote electrode 168 having an electrical potential. The chip 152 can allow for minimizing interference between the electrical potential of the external media 156 and the pressure sensing components 154. As in the illustrated embodiment, the substrate 158 can have P-type conductivity, the isolation area 160 can have n-type conductivity, and the pressure sensing component 154 can be a P-type piezoresistor configured to sense pressure. The media 156 can include any of a variety of media, such as a tissue of a patient or a bodily fluid of a patient.

A sidewall 166 of the chip 152 can be formed, for example, as a result of mechanical sawing or laser dicing. Die side walls after dicing are protected only by a very thin native oxide that can fail to protect the substrate 158 from an electrical potential of the external media 156. In case of conductive media 156 and the presence of a remote electrode 168, an electrical current can flow through the media 156. The substrate 158, e.g., the sidewall 166 thereof, can be configured to directly contact the conductive media 156 so as to allow direct electrical communication between the chip 152 and the conductive media 156. Edges of the sidewall 166 can be doped with boron or phosphorus (not shown), which can allow for isolation. This type of isolation can be practical when thickness of the chip's device layer is below about 15 μm or below about 10 μm. Otherwise, time required to form the isolation area by diffusion can be prohibitively long.

Higher potential can be applied to the isolation area 160 than to the substrate 158 and to the pressure sensitive components 154 in order to have both the p-n junction 162 between the isolation area 160 and the substrate 158 and the p-n junction 164 between the isolation area 160 and the sensitive component 154 be closed. For example, a potential, e.g., a 3 V potential, can be applied to the isolation area 160, the substrate area 158 can be grounded, and the pressure sensitive components 154 can be operating in way such that the highest potential is not greater than the potential applied to the isolation area 160. In a case when external media potential is lower than the substrate 158 potential, there may be a charge transfer to the substrate 158. However, this charge transfer will not result in any additional current in the sensor circuit because the substrate 158 is isolated from the pressure sensitive components 154 with the p-n junction 162. In a case where the electrical potential of the external media 156 is higher than the applied potential, the p-n junction 162 can open and a current can start to flow between the isolation area 160 and the external media 156. However, even in this case, the pressure sensitive components 154 will not be affected because the pressure sensitive components 154 are isolated from the isolation area 160 by the reverse-biased p-n junction 164.

Different electrical connections to the isolation area 160 and to the sensitive component 154 can be used. For example, these connections can be combined as shown in FIG. 12, discussed further below, or these connections can be provided independently using different wires.

FIG. 12 shows a schematic representation of FIG. 11 as an electrical circuit, thereby demonstrating the isolation area's prevention of parasitic electrical current flow to the conductive media 156. In general, the remote electrode 168 corresponds to a first node 168 in FIG. 12 having a first potential/voltage, the conductive media 156 corresponds to a first resistor 156 in FIG. 12, the sidewall 166 corresponds to a second node having a second potential/voltage, the substrate 158 corresponds to a second resistor 158 in FIG. 12, the first p-n junction 162 corresponds to a first diode 162 in FIG. 12, the second p-n junction 164 between the sensitive component 154 and the isolation area 160 corresponds to a second diode 164 in FIG. 12, a third node 172 located between the first and second diodes 162, 164 represents a contact to the isolation area 160 that is connected to a fourth node 174 having a third potential/voltage, and bridge resistance 170 of the sensor 154 corresponds to a third resistor 170 in FIG. 12. The third potential/voltage is a voltage applied to the resistor 170 in FIG. 12 representing a sensing component 154 in FIG. 11. Thus, the first diode 162 can only be open when the first potential/voltage of the first node 166 is greater than a potential/voltage at the third node 172. In other words, the first diode 162 can only be open when the potential/voltage of the remote electrode 168 is greater than the potential/voltage applied to the resistor 170, which is the third potential/voltage at the fourth node 174. Because the third node 172 is connected to the fourth node 174, the second diode 164 is always closed. Parasitic electrical current flow from the substrate 158 to the conductive media 156 is thus prevented due to the presence of the isolation area 160. Abnormal potential of the substrate 158 can be detected by an increase of the current supplied through the fourth node 174.

In this way, when the chip is in direct contact with conductive media, such as in a medical application when the chip is disposed within a catheter tube with fluid surrounding the tube in direct contact with the chip, the chip can be prevented from passing electrical current to the fluid and hence to a patient having the catheter therein. The patient can thereby be more safely treated with reduced risk of injury caused by parasitic electricity.

Figure 13:
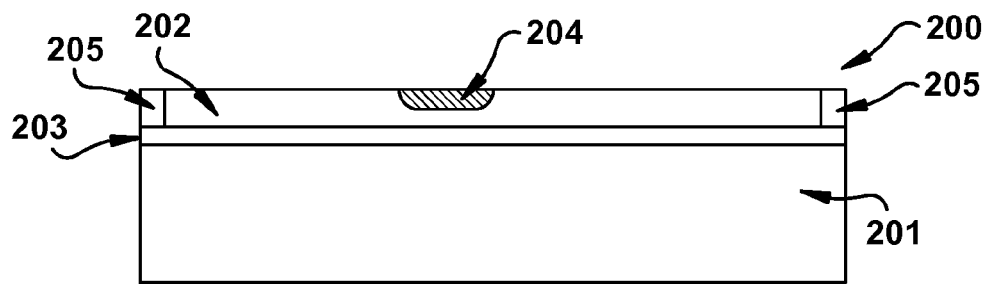
FIG. 13 is a side cross-sectional view of another embodiment of a sensor chip.

FIG. 13 shows another embodiment of a semiconductor sensor chip 200. Generally, the chip 200 can be configured as a sensing device formed on a silicon on insulator (SOI) substrate and can have an isolation area that can protect the sensor circuit from electrical potential of external media. The chip 200 can include a handle layer 201, a device layer 202, a dielectric layer 203, a pressure sensing component 204 such as a sensor resistor, and an isolation area 205. The device layer 202 can have a top side and side walls, the top side and the side walls being configured to contact an external media (not shown). The device layer 202 can have the isolation area 205 formed therein along the side walls. A remainder portion of the device layer 202, e.g., a portion excluding the pressure sensing component 204 and the isolation area 205, can define a body of the device layer 202. The dielectric layer 203 can be configured to electrically isolate the device layer 202 from the handle layer 201. The dielectric layer 203 can be a layer of silicon dioxide, also referred as buried oxide or BOX.

The pressure sensing component 204 can have a first type of conductivity (e.g., p-type conductivity), the isolation area 205 can have the first type of conductivity, and the body of the device layer 202 can have a second type of conductivity (e.g., n-type conductivity). A first p-n junction can be formed between the isolation area 205 and the body of the device layer 202. A second p-n junction can be formed between the sensor resistor 204 and the body of the device layer 202. Similar to that discussed above, the side walls of the device layer 202 are not protected with a dielectric layer (native oxide does not provide required protection), and the side walls can be in contact with an external media. The external media can have an electrical potential. Also similar to that discussed above, a combination of the first p-n junction, the second p-n junction, and the dielectric layer 203 that separates the device layer 202 and the handle layer 201 can be configured to provide electrical isolation of the pressure sensing component 204 from the electrical potential of the external media when the device layer 202 is in contact with the external media.

The features disclosed herein with respect to any particular embodiment can be combined with or incorporated into any other embodiment.

In the present disclosure, like-named components of the embodiments generally have similar features, and thus within a particular embodiment each feature of each like-named component is not necessarily fully elaborated upon.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A sensing device, comprising:
   a catheter die including
      a top side and a bottom side defining a thickness of the catheter die,
      a first side and a second side defining a width of the catheter die, each of the first and second sides extending between the top and bottom sides,
      a first end and a second end defining a length of the catheter die,
      a sensor component located on the top side,
      a first bond pad on the top side, the first pad being electrically connected to the sensor component and having a first wire attached thereto,
      a second bond pad on the bottom side, the second pad being electrically connected to the sensor component and having a second wire attached thereto, the electrical connections of the first and second wires being configured to facilitate sensing functionality of the sensor component, and
      a through-silicon via extending between the bottom and top sides and electrically connected to the first and second pads.

2. The sensing device of claim 1, wherein the catheter die further includes a third bond pad on one of the bottom and top sides, the third pad having a third wire attached thereto, an electrical connection of the third wire being configured to facilitate sensing functionality of the sensor component.

3. The sensing device of claim 2, wherein the catheter die further includes a fourth bond pad on one of the bottom and top sides, the fourth pad having a fourth wire attached thereto, an electrical connection of the fourth wire being configured to facilitate sensing functionality of the sensor component.

4. The sensing device of claim 3, wherein each of the first, second, third, and fourth wires are connected to their respective bond pads using one or more of wire bonding, thermocompression, conductive adhesive, welding, and soldering.

5. The sensing device of claim 3, wherein the third pad is on the top side and the fourth pad is on the bottom side, the catheter die further comprising a second through-silicon via extending between the bottom and top sides and electrically connected to the third and fourth pads.

6. The sensing device of claim 3, wherein sensor components connected to the first, second, third, arid fourth wires form a full Wheatstone bridge.

7. The sensing device of claim 3, wherein the third and the fourth pads are on a same one of the top and bottom sides.

8. The sensing device of claim 1, wherein the first pad has a longitudinal length of the first wire attached thereto with the longitudinal length of the first wire extending longitudinally along a portion of the length of the catheter die, and the second pad has a longitudinal length of the second wire attached thereto with the longitudinal length of the second wire extending longitudinally along a portion of the length of the catheter die.

9. The sensing device of claim 8, wherein the longitudinal lengths of each of the first and second wires are connected to their respective bond pads using one or more of wire bonding, therrnocompression, conductive adhesive, welding, and soldering.

10. The sensing device of claim 1, wherein the sensor component includes at least one of a solid-state resistor, a thin-film resistor, a bipolar transistor, a metal oxide semiconductor (MOS) transistor, a unipolar transistor, a thin-film transistor, a diode, a complementary metal oxide semiconductor (CMOS) transistor pair, a p-n junction, a capacitor, a thin film capacitor, an inductor, and a thin film inductor.

11. The sensing device of claim 1, wherein the sensor component is selected from the group consisting of a stress sensor, a pressure sensor, a temperature sensor, a pH sensor, a chemical sensor, a magnetic sensor, a radiation sensor, and a photosensor.

12. The device of claim 11, wherein the sensor component includes at least two of the stress sensor, the pressure sensor, the temperature sensor, the pH sensor, the chemical sensor, the magnetic sensor, the radiation sensor, and the photosensor.

13. The sensing device of claim 1, further comprising a catheter tube having the catheter die disposed in a lumen extending through the catheter tube, the first and second wires having tail portions extending off the catheter die and extending longitudinally within the lumen.

14. The sensing device of claim 13, wherein the length of the catheter die is greater than a diameter of the lumen, the width of the catheter die is less than the diameter of the lumen, and the thickness of the catheter die is less than the diameter of the lumen.

15. The sensing device of claim 8, wherein one or both of the first and second wires are soldered to their respective bond pads using a solder composition selected from the group of compositions consisting of Au—In, Au—Sn, Cu—Sn, Al—Ge.

16. The sensing device of claim 1, wherein the first bond pad is connected to a first sensor contact and the second bond pad is connected to a second sensor contact.

* * * * *